US006649737B1

(12) United States Patent
Hillman et al.

(10) Patent No.: US 6,649,737 B1
(45) Date of Patent: Nov. 18, 2003

(54) HUMAN GALACTOSYLTRANFERASES

(75) Inventors: Jennifer L. Hillman, Mountain View, CA (US); Karl J. Guegler, Menlo Park, CA (US); Neil C. Corley, Mountain View, CA (US); Purvi Shah, Sunnyvale, CA (US); Chandra Patterson, Mountain View, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/373,902

(22) Filed: Aug. 12, 1999

Related U.S. Application Data

(62) Division of application No. 09/055,097, filed on Apr. 3, 1998, now Pat. No. 5,955,282.

(51) Int. Cl.$^7$ .............................................. C07K 14/00
(52) U.S. Cl. .................... 530/350; 536/23.1; 514/2; 424/185.1
(58) Field of Search ........................... 530/350; 514/2; 536/23.1; 424/185.1

(56) References Cited

PUBLICATIONS

Goode, S. et al., "The neurogenic genes egghead and brainiac define a novel signaling pathway essential for epithelial morphogenesis during Drosophila oogenesis", *Development*, 122: 3863–3879 (1996).
Lodish, H. et al., *Molecular Cell Biology*, Scientific American Books, New York, N.Y., pp. 196–197, 623–624, 1167–1172 (1995).
Gumbiner, B.M., "Epithelial Morphogenesis", *Cell*, 69: 385–387 (1992).
Watson, K.L. et al., "Drosophila in cancer research: the first fifty tumor suppersor genes", *J. Cell Sci. Suppl.*, 18: 19–33 (1994).
Morisato, D. And K.V. Anderson, "Signaling Pathways That Establish the Dorsal–Ventral Pattern of the Drosophila Embryo", *Annu. Rev. Genetics*, 29: 371–399 (1995).
Goode, S. et al., "The neurogenic locus brainiac cooperates with the Drosophila EGF receptor to establish the ovarian follicle and to determine its dorsal–ventral polarity", *Development*, 116: 177–192 (1992).
Goode, S. et al., "brainiac Encodes a Novel, Putative Secreted Protein That Cooperates with Grk TGFα in the Genesis of the Follicular Epithelium", *Developmental Biol.*, 178: 35–50 (1996).
Yuan, Y.P. et al., "Secreted Fringe–like Signaling Molecules May Be Glycosyltransferases", *Cell*, 89: 9–11 (1997).
Hennet, et al., "Genomic Cloning and Expression of Three Murine UDP–galactose: β–N–Acetyglucosamine γ1,3–Galactosyltransferase Genes", *J. Biol. Chem.*, 273: 58–65 (1998).

Kolbinger, F. et al., "Cloning of a Human UDP–galactose:2–Acetamido–2–deoxy–D–glucose 3β–Galactosyltransferase Catalyzing the Formation of Type 1 Chains", *J. Biol. Chem.*, 273: 433–440 (1998).
Yadav, S. and K. Brew, "Identification of a Region of UDP–galactose: N–Acetylglucosamine β4–Galactosyltransferase Involved in UDP–galactose Binding by Differential Labeling", *J. Biol Chem.*, 265: 14163–14169 (1990).
Yadav, S.P. and K. Brew, "Structure and Function in Galactosyltransferase", *J. Biol. Chem.*, 266: 698–703 (1991).
Shaper, N.L. et al., "The Chicken Genome Contains Two Functional Nonallelic β1,4–Galactosyltransferase Genes", *J. Biol. Chem.*, 272: 31389–31399 (1997).
Shur, B.D., "Glycosyltransferases as cell adhesion molecules", *Curr. Opin. Cell Biol.*, 5: 854–863 (1993).
Uejima, T. et al., "Complementary DNA Cloning for Galactosyltransferase Associated with Tumor and Determination of Antigenic Epitopes Recognized by Specific Monoclonal Antibodies", *Cancer Res.*, 52: 6158–6163 (1992).
Paulson, J.C. and K.J. Colley, "Glycosyltransferases", *J. Biol. Chem.*, 264: 17615–17618 (1989).
Etienne–Decerf, J. et al., "Elevated anti–α–galactosyl antibody titres. A Marker of progression in autoimmune thyroid disorders and in endocrine ophthalmopathy?", *Endocrinol.*, 115: 67–74 (1987).
Hiller et al. Genbank Accession No. H20623.
Hiller et al. Genbank Accession No. N63041.
Jansen, M. Pediatric Res. 37(6):681–686, 1995.*
Reiger. Glossary of Genetics & Cystogenetics, Classical & Mol. 4$^{th}$ ed., Springer–Verlag, Berlin, p. 17, 1976.*
MPSRCH Search Report, p. 2–3, MPSRCH Search Report, p. 5, 2001.*
Alberts et al. Mol. Biol. Cell, 3$^{rd}$ ed., p. 465, 1994.*
Shantz et al. Intl. J. Biochem. Cell. Biol. 31: 107–122, 1999.*
McClean et al. Eur. J. Cancer, 29A: 2243–2248, 1993.*
Fu et al. EMBO J. 15: 4392–4401, 1996.*
Bowie et al. Science, 257: 1306–1310, 1990.*
Burgers et al. J. Cell Biol. 111: 2129–2138, 1990.*
Lazak et al. Mol. Cell Biol. 8: 1247–1252, 1988.*
Bork, Genome Res. 10: 398–400, 2000.*
Scott et al. Nature Genetics, 21:440–443, 1999.*
Jain, Sci. Am. 271: 58–65, 1994.*
Gura Science, 1041–1042, 1997.*
Curti, Crit. Rev. Oncol/Hematol. 14: 29–39, 1993.*
Hartwell, Science, 278: 1064–1068, 1997.*
Tao, J. Immunol. 143(8): 2595–2601, 1989.*

(List continued on next page.)

Primary Examiner—Susan Ungar
Assistant Examiner—Minh Tam Davis
(74) Attorney, Agent, or Firm—Incyte Genomics, Inc.

(57) ABSTRACT

The invention provides human galactosyltransferases (HUGA) and polynucleotides which identify and encode HUGA. The invention also provides expression vectors, host cells, antibodies, agonists, and antagonists. The invention also provides methods for diagnosing, treating, or preventing disorders associated with expression of HUGA.

3 Claims, 16 Drawing Sheets

OTHER PUBLICATIONS

Gillies Human Antibodies Hybridomas 1(1):47–54, 1990.*

Berger et al. Genbank—Accession No. AAR28838, 1992.*

MPSRCH Search Report, p. 7–8.*

Johnstone et al. Immunochemistry In Practice, 2$^{nd}$ ed, Blackwell Sci: Publ., Oxford, p. 49–50, 1987.*

Kleene, R. et al., "Expression of Soluble Active Human β1, 4 Galactosyltransferase in *Saccharomyces cerevisiae*", *Biochemical and Biophysical Research Communications*, 201(1): 160–167 (1994).

Schwientek, T. and J.F. Ernst, "Efficient intra–and extracellular production of human β1, 4–galactosyltransferase in *Saccharomyces cerevisiae* is mediated by yeast secretion leaders", *Gene*, 145: 299–303 (1994).

Sherwood, A.L. et al., "Stable Expression of a cDNA Encoding a Human β1→ 3Galactosyltransferase Responsible for Lacto–Series Type 1 Core Chain Synthesis in Non–Expressing Cells: Variation in the Nature of Cell Surface Antigens Expressed", *Journal of Cellular Biochemistry*, 50: 165–177 (1992).

Amado, M. et al., "A Family of Human β3–Galactosyltransferases: Characterization of Four Members of a UDP–Galactose:β–N–Acetyl–Glucosamine/β–N–Acetyl–Galactosamine β–1, 3–Galactosyltransferase Family", *Journal of Biological Chemistry*, 273(21): 12770–12778 (1998).

Database EMBL Nucleotide and Protein Sequences, Aug. 10, 1998, XP002109787, Hinxton, GB AC = AL031228. Human DNA sequence from clone 1033B10 on chromosome 6p21.2–21–31; contains the gene for GalT3. (beta3–Galactosyltransferase).

* cited by examiner

```
5' CGG CTC GAG CTT ACG GAT CCC CTC GGA GTA CGC CGC ACC ATG CAG CTC AGG CTC
                     9           18           27           36       45      54
                                                              M   Q   L   R   L

TTC CGG CGC CTC CTT GCC GCT TTG CTG CTG TTG GTG ATC GTC TGG ACC CTC TTC
                    63           72           81           90           99      108
     F   R   R   L   L   A   A   L   L   L   L   V   I   V   W   T   L   F

GGG CCT TCG GGG TTG GGA GAG GAG CTG CTC TCA AGC CTC TCA CTA GCC TCC CTG CTC
                   117          126          135          144          153     162
     G   P   S   G   L   G   E   E   L   L   S   S   L   S   L   A   S   L   L

CCA GCC CCC GCC TCA CCG GGG CCG CCC CTG GCC CTG CCC CGC CTC TTG ATC CCC
                   171          180          189          198          207     216
     P   A   P   A   S   P   G   P   P   L   A   L   P   R   L   L   I   P

AAC CAG GAA GCT TGC AGT GGT CCC GGG GCC CCT CCC TTC CTG CTC ATC CTG GTG
                   225          234          243          252          261     270
     N   Q   E   A   C   S   G   P   G   A   P   P   F   L   L   I   L   V

TGC ACG GCT CCG GAG AAC CTG AAC CAG AGA AAC GCC ATT CGG GCT TCG TGG GGC
                   279          288          297          306          315     324
     C   T   A   P   E   N   L   N   Q   R   N   A   I   R   A   S   W   G

GGG CTG CGC GAG GCC CGG GGG CTC AGG GTA CAG ACG CTA TTC TTG CTG GGA GAG
                   333          342          351          360          369     378
     G   L   R   E   A   R   G   L   R   V   Q   T   L   F   L   L   G   E
```

FIGURE 1A

```
    387         396         405         414         423         432
CCG AAC GCA CAG CAC CCC GTG TGG GGT TCC CAG GGG AGT GAC CTG GCC TCG GAG
 P   N   A   Q   H   P   V   W   G   S   Q   G   S   D   L   A   S   E 441         450         459         468         477         486
TCA GCA GCC CAG GGG GAT ATC TTG CAG GCC GCC TTC CAG GAC TCC TAC CGC AAC
 S   A   A   Q   G   D   I   L   Q   A   A   F   Q   D   S   Y   R   N 495         504         513         522         531         540
CTC ACC CTA AAG ACC CTC AGC GGG CTG AAC TGG GCT GAG AAA CAC TGC CCC ATG
 L   T   L   K   T   L   S   G   L   N   W   A   E   K   H   C   P   M 549         558         567         576         585         594
GCC CGA TAC GTC CTC AGC GAC ACG GAC GAT GAT GTG TAT GTC AAC GTC CCT GAA CTG
 A   R   Y   V   L   S   D   T   D   D   D   V   Y   V   N   V   P   E   L 603         612         621         630         639         648
GTA TCA GAG CTG GTC TTG CGA GGG GGC CGT TGG GGG CAA TGG GAG AGA AGC ACG
 V   S   E   L   V   L   R   G   G   R   W   G   Q   W   E   R   S   T 657         666         675         684         693         702
GAA CCC CAG AGA GAG GCT GAG CAG GAA GGA GGC CAG GTT TTG CAC AGC GAG GAA
 E   P   Q   R   E   A   E   Q   E   G   G   Q   V   L   H   S   E   E 711         720         729         738         747         756
GTG CCT CTT CTG TAC TTG GGC CGG GTG CGC GTG CAC TGG CGG GTG AAC CCC TCT CGG ACA
 V   P   L   L   Y   L   G   R   V   R   V   H   W   R   V   N   P   S   R   T
```

FIGURE 1B

```
      765            774            783            792            801            810
CCG GGG AGG CAC CGC GTA TCA GAG GAG CAG TGG CCT CAC ACC TGG GGC CCC
 P   G   R   H   R   V   S   E   E   Q   W   P   H   T   W   G   P 819            828            837            846            855            864
TTT CCA CCC TAT GCC TCA GGC ACG GGG TAT GTG CTG TCA GCG TCT GCT GTG CAG
 F   P   P   Y   A   S   G   T   G   Y   V   L   S   A   S   A   V   Q 873            882            891            900            909            918
CTC ATT CTC AAG GTG GCC AGC CGG GCA CCC CTT CTC CCA TTA GAG GAT GTC TTT
 L   I   L   K   V   A   S   R   A   P   L   L   P   L   E   D   V   F 927            936            945            954            963            972
GTG GGG GTA AGT GCC CGA CGA GGA GGC CTC GCC CCA ACA CAG TGT GTC AAG CTG
 V   G   V   S   A   R   R   G   G   L   A   P   T   Q   C   V   K   L 981            990            999           1008           1017           1026
GCT GGT GCC ACC CAC TAC CCG CTA GAC CGG TGC TGC TAT GGG AAA TTC CTG CTG
 A   G   A   T   H   Y   P   L   D   R   C   C   Y   G   K   F   L   L 1035           1044           1053           1062           1071           1080
ACG TCC CAC AGG CTG GAC CCC TGG AAG ATG CAG GAA GCC TGG AAG CTG GTG GGT
 T   S   H   R   L   D   P   W   K   M   Q   E   A   W   K   L   V   G 1089           1098           1107           1116           1125           1134
GGC TCT GAC GGG GAA AGG ACT GCG CCC TTT TGC TCC TGG TTC CAG GGA GTC CTG
 G   S   D   G   E   R   T   A   P   F   C   S   W   F   Q   G   V   L
```

FIGURE 1C

```
      1143            1152            1161           1170           1179          1188
GGC ATC CTG CGG TGT CGA GCA ATA GCC TGG CTT CAG AGC TGA GAG TGC CTG GGG
 G   I   L   R   C   R   A   I   A   W   L   Q   S 1197            1206            1215           1224           1233          1242
CCA CAG GAA AGG CAG GAA CAG GAC CTT CTC TCT CCC AGG CCC AAC GCA GGG GCC 1251            1260            1269           1278           1287          1296
CTC ACT GGC TGC AGC TGA TCT GTT TCC TTA TAC CAG ATC CTC AGT CTC ACT AAA 1305            1314            1323           1332           1341          1350
GAC AGC GAT ATG GGA GAC ACC CAG GGG CCT GGC CCG CCA GCC CAA AAG ATG GTC 1359            1368            1377           1386           1395          1404
ATC GGG AAG AGA AAA AGA AAA TGC TGC AGT TGT TCT CTC AAG CTA GGG CAG 1413            1422            1431
AAG AGG GGT GTC AAC TCC TCA ATA AAA TTT  3'
```

FIGURE 1D

```
       11            20            29            38            47            56
5'GT GGA TTT CCA CGG CTC TTG CCC AGA GGC GGG TAC ACT GTG TTC CAA TGT GCC ACG 65            74            83            92           101           110
GAA CTC ACG CAG TGG CAC TTT GTG GCT TCA TGA AGG AAG AGG CAG GCC ACG CAA 119           128           137           146           155           164
CAC TTC CTC CCC AAG CCA AGG AGA AGT ATC ACT TTT AGA GGC AGA GGA GCG GAA 173           182           191           200           209           218
GGC AGT GGG TGT GAC CAA AAG TGC CAT TTG TTA AAG CTT ATC TTC CTT GCC AGA 227           236           245           254           263           272
TTT TAA AAA CTA TTA TGG AAA ATC TCA AGC ATT CAC AAA AGT AGA GAG AAA GAA 281           290           299           308           317           326
AGG ACT CTC AGA CTG GAG CAG AAC TAC TGA GAA AAA CCA GGC ATT GTA TCT 335           344           353           362           371           380
TCA GTT GTC ATC AAG TTC GCA ATC AGA TTG GAA AAG CTC AAC TTG AAG CTT TCT
```

FIGURE 2A

```
       389             398             407             416             425             434
TGC CTG CAG TGA AGC AGA GAG ATA GAT ATT ATT CAC GTA ATA AAA AAC ATG GGC
                                                                         M   G 443             452             461             470             479             488
TTC AAC CTG ACT TTC CAC CTT TCC TAC AAA TTC CGA TTA CTG TTG CTG TTG ACT
 F   N   L   T   F   H   L   S   Y   K   F   R   L   L   L   L   L   T 497             506             515             524             533             542
TTG TGC CTG ACA GTG GTT GGG TGG GCC ACC AGT AAC TAC TTC GTG GGT GCC ATT
 L   C   L   T   V   V   G   W   A   T   S   N   Y   F   V   G   A   I 551             560             569             578             587             596
CAA GAG ATT CCT AAA GCA AAG GAG TTC ATG GCT AAT TTC CAT AAG ACC CTC ATT
 Q   E   I   P   K   A   K   E   F   M   A   N   F   H   K   T   L   I 605             614             623             632             641             650
TTG GGG AAG GGA AAA ACT CTG ACT AAT GAA GCA TCC ACG AAG AAG GTA GAA CTT
 L   G   K   G   K   T   L   T   N   E   A   S   T   K   K   V   E   L 659             668             677             686             695             704
GAC AAC TGT CCT TCT GTG TCT CCT TAC CTC AGA GGC CAG AGC AAG CTC ATT TTC
 D   N   C   P   S   V   S   P   Y   L   R   G   Q   S   K   L   I   F 713             722             731             740             749             758
AAA CCA GAT CTC ACT TTG GAA GAG GTA CAG GCA GAA AAT CCC AAA GTG TCC AGA
 K   P   D   L   T   L   E   E   V   Q   A   E   N   P   K   V   S   R
```

FIGURE 2B

```
      767             776             785             794             803             812
GGC CGG TAT CGC CCT CAG GAA TGT AAA GCT TTA CAG AGG GTC GCC ATC CTC GTT
 G   R   Y   R   P   Q   E   C   K   A   L   Q   R   V   A   I   L   V 821             830             839             848             857             866
CCC CAC CGG AAC AGA GAG AAA CAC CTG ATG TAC CTG CTG GAA CAT CTG CAT CCC
 P   H   R   N   R   E   K   H   L   M   Y   L   L   E   H   L   H   P 875             884             893             902             911             920
TTC CTG CAG AGG CAG CAG CTG GAT TAT GGC ATC TAC GTC ATC CAC CAG GCT GAA
 F   L   Q   R   Q   Q   L   D   Y   G   I   Y   V   I   H   Q   A   E 929             938             947             956             965             974
GGT AAA AAG TTT AAT CGA GCC AAA CTC TTG AAT GTG GGC TAT CTA GAA GCC CTC
 G   K   K   F   N   R   A   K   L   L   N   V   G   Y   L   E   A   L 983             992             1001            1010            1019            1028
AAG GAA GAA AAT TGG GAC TGC TTT ATA TTC CAC GAT GTG GAC CTG GTA CCC GAG
 K   E   E   N   W   D   C   F   I   F   H   D   V   D   L   V   P   E 1037            1046            1055            1064            1073            1082
AAT GAC TTT AAC CTT TAC AAG TGT GAG GAG CAT CCC AAG CAT CTG GTG GTT GGC
 N   D   F   N   L   Y   K   C   E   E   H   P   K   H   L   V   V   G 1091            1100            1109            1118            1127            1136
AGG AAC AGC ACT GGG TAC AGG TTA CGT TAC AGT GGA TAT TTT GGG GGT GTT ACT
 R   N   S   T   G   Y   R   L   R   Y   S   G   Y   F   G   G   V   T
```

FIGURE 2C

```
                    1145           1154           1163           1172           1181           1190
                    GCC CTA AGC AGA GAG CAG TTT TTC AAG GTG AAT GGA TTC TCT AAC AAC TAC TGG
                     A   L   S   R   E   Q   F   F   K   V   N   G   F   S   N   N   Y   W 1199           1208           1217           1226           1235           1244
                    GGA TGG GGA GGC GAA GAC GAT GAC CTC AGA CTC AGG GTT GAG CTC CAA AGA ATG
                     G   W   G   G   E   D   D   D   L   R   L   R   V   E   L   Q   R   M 1253           1262           1271           1280           1289           1298
                    AAA ATT TCC CGG CCC CTG CCT GAA GTG GGT AAA TAT ACA ATG AAG CTC TTC CAC ACT
                     K   I   S   R   P   L   P   E   V   G   K   Y   T   M   K   L   F   H   T 1307           1316           1325           1334           1343           1352
                    AGA GAC AAA GGC AAT GAG GTG AAC GCA GAA CGG ATG AAG CTC TTA CAC CAA GTG
                     R   D   K   G   N   E   V   N   A   E   R   M   K   L   L   H   Q   V 1361           1370           1379           1388           1397           1406
                    TCA CGA GTC TGG AGA ACA GAT GGG TTG AGT AGT TGT TCT TAT AAA TTA GTA TCT
                     S   R   V   W   R   T   D   G   L   S   S   C   S   Y   K   L   V   S 1415           1424           1433           1442           1451           1460
                    GTG GAA CAC AAT CCT TTA TAT ATC AAC ATC ACA GTG GAT TTC TGG TTT GGT GCA
                     V   E   H   N   P   L   Y   I   N   I   T   V   D   F   W   F   G   A 1469           1478           1487           1496           1505           1514
                    TGA CCC TGG ATC TTT TGG TGA TGT TTG GAA GAA CTG ATT CTT TGT TTG CAA TAA
```

FIGURE 2D

```
     1523      1532      1541      1550      1559      1568
TTT TGG CCT AGA GAC TTC AAA TAG TAG CAC ACA TTA AGA ACC TGT TAC AGC TCA 1577      1586      1595      1604      1613      1622
TTG TTG AGC TGA ATT TTT CCT TTT TGT ATT TTC TTA GCA GAG CTC CTG GTG ATG 1631      1640      1649      1658      1667      1676
TAG AGT ATA AAA CAG TTG TAA CAA GAC AGC TTT CTT AGT CAT TTT GAT CAT GAG 1685      1694      1703      1712      1721      1730
GGT TAA ATA TTG TAA TAT GGA TAC TTG AAG GAC TTT ATA TAA AAG GAT GAC TCA 1739      1748      1757      1766      1775      1784
AAG GAT AAA ATG AAC GCT ATT TGA GGA CTC TGG TTG AAG GAG ATT TAT TTA AAT 1793      1802      1811      1820      1829      1838
TTG AAG TAA TAT ATG GGA TAA AAG GCC ACA GGA AAT AAG ACT GCT GAA TGT 1847      1856      1865      1874      1883      1892
CTG AGA GAA CCA GAG TTG TTC TCG TCC AAG GTA GAA AGG TAC GAA GAT ACA ATA
```

FIGURE 2E

```
           1901        1910        1919        1928        1937        1946
           CTG TTA TTC ATT TAT CCT GTA CAA TCA TCT GTG AAG TGG TGT CAG GTG AGA 1955        1964        1973        1982        1991        2000
           AGG CGT CCA CAA AAG AGG GGA GAA AAG GCG ACG AAT CAG GAC ACA GTG AAC TTG 2009        2018        2027        2036        2045        2054
           GGA ATG AAG AGG TAG CAG GAG GGT GGA GTG TCG GCT GCA AAG GCA GCA GTA GCT 2063        2072        2081        2090        2099        2108
           GAG CTG GTT GCA GGT GCT GAT AGC CTT CAG GGG AGG ACC TGC CCA GGT ATG CCT 2117        2126        2135        2144        2153        2162
           TCC AGT GAT GCC CAC CAG AGA ATA CAT TCT CTA TTA GTT TTT AAA GAG TTT TTG 2171        2180        2189        2198        2207        2216
           TAA AAT GAT TTT GTA CAA GTA GGA TAT GAA TTA GCA GTT TAC AAG TTT ACA TAT 2225        2234        2243        2252        2261        2270
           TAA CTA ATA ATA AAT ATG TCT ATC AAA TAC CTC TGT AGT AAA ATG TGA AAA AGC
```

FIGURE 2F

2279 AAA AAA AAA A 3'

FIGURE 2G

```
1    MQLRFRRLLAAL-LLVIWTLF--------                     1705085
1    MQSK-HRKLLLR--CLLVLPLILLV----                     GI 1150971
1    MASKVSCLYVLSVVCWASALWYLSITRPTS                    GI 2745735

24   ---GP-SGLGEELLSLS-LASLLPAPASPG                    1705085
23   DYCGLLTHLHELNFERHFHYPLNDDTGSGS                    GI 1150971
31   SYTGS-KPFSHLTVARK-NFTFGNIRTRPI                    GI 2745735

49   PPLALPRL--LIPNQEACSGPGAPPF-LLI                    1705085
53   ASSGLDKFAYLRVPSFTAEVPVDQPARLTM                    GI 1150971
59   NPHSFE-F--LINEPNKCE--KNIPF-LVI                    GI 2745735

76   LVCTAPENLNQRNAIRASWGGLREARGLRV                    1705085
83   LIKSAVGNSRRREAIRRTWGYEGRFSDVHL                    GI 1150971
83   LISTTHKEFDARQAIRETWGDENNFKGIKI                    GI 2745735

106  QTLFLLGEPNAQHPVWGSQGSDLASESAAQ                    1705085
113  RRVFLLGTAEDSE----KDVAWESREH                       GI 1150971
113  ATLFLLG--KNADPVLNQM--VEQESQIF                     GI 2745735

136  GDILQAAFQDSYRNLTLKTLSGLNWAEKHC                    1705085
136  GDILQADFTDAYFNNTLKTMLGMRWASEQF                    GI 1150971
138  HDIIVEDFIDSYHNLTLKTLMGMRWVATFC                    GI 2745735
```

```
1    MGFNLTFHLSYKFRLLLLTLCLTVVGWAT                       2551161
1    MKEPALPGTSLQRACRLLVAFCALHLSATL                      GI 1469908

31   SNYFVGAIQEIPKAKEFMANFHKTLILG--                      2551161
31   LYYLAGSSLTPPRSPEPPPRRPPPPANLSLP                     GI 1469908

59   -------KGKTLTNEASTKKVELDN----                       2551161
61   PSRPPPPAARPRPGPVSAQPRNLPDSAPS                       GI 1469908

77   --CPSVSPYLRGQSKLIFKPDLTLEEVQAE                      2551161
91   GLCPDPSPLLVGPLRVEFSQPVNLEEVAST                      GI 1469908

105  NPKVSRG-RYRPQECKALQRVAILVPHRNR                      2551161
121  NPEVREGGRFAPKDCKALQKVAIIIPFRNR                      GI 1469908

134  EKHLMYLLEHLHPFLQRQQLDYGIYVIHQA                      2551161
151  EEHLKYWLYYMHPILQRQQLDYGVYVINQD                      GI 1469908

164  EGKKFNRAKLLNVGYLEALKEENWDCFIFH                      2551161
181  GDEEFNRAKLLNVGFTEALKEYDYDCFVFS                      GI 1469908

194  DVDLVPENDFNLYKCEEHPKHLVVGRNSTG                      2551161
211  DVDLIPMDDRNTYKCYSQPRHLSVSMDKFG                      GI 1469908
```

HUMAN GALACTOSYLTRANFERASES

This application is a divisional application of U.S. application Ser. No. 09/055,097, filed Apr. 3, 1998 now U.S. Pat. No. 5,955,282.

FIELD OF THE INVENTION

This invention relates to nucleic acid and amino acid sequences of human galactosyltransferases and to the use of these sequences in the diagnosis, treatment, and prevention of cancer, developmental disorders, reproductive disorders, and autoimmune/inflammatory disorders.

BACKGROUND OF THE INVENTION

Epithelia, composed of sheets of highly differentiated epithelial cells, cover almost all internal and external body and organ surfaces, such as those of the intestine, kidney, pancreas, lung, mouth, and cervical tract. Epithelia regulate the exchange of substances between tissue compartments and with the outside environment. Regulated changes in embryonic epithelial cell arrangement and shape lead to the formation of internal organs. Secreted and membrane-bound proteins produced by the mesenchyme regulate these changes. It is hypothesized that regulation of cell/cell adhesion and cell motility plays an important role in epithelial morphogenesis. (Goode, S. et al. (1996) Development 122:3863–3879; Lodish, H. et al. (1995) *Molecular Cell Biology*, Scientific American Books, New York, N.Y. pp. 196–197, 623–624, 1167–1172; and Gumbiner, B. M. (1992) Cell 69:385–387.)

The follicular epithelium of the fruitfly *Drosophila melanogaster* has been used as a model system for epithelial morphogenesis. Drosophila is a useful system in which to study growth, differentiation, and tumor suppression as many of its genes have mammalian homologs. (Watson, K. L. et al. (1994) J. Cell Sci. Suppl. 18:19–33; and Lodish, supra., pp. 1167–1172.) The follicular epithelium, a monolayer of somatic cells that develops along with the germline during oogenesis, completely surrounds each developing egg chamber and eventually secretes components of the eggshell. Both the follicular epithelium and the oocyte have distinct dorsal-ventral asymmetry established by the interaction of at least 13 genes, some expressed in the follicle and some in the oocyte. Mutations in these genes lead to either dorsalization or ventralization of the eggshell and embryo. (Morisato, D. and Anderson, K. V. (1995) Annu. Rev. Genetics 29:371–399.)

Brainiac, a gene important for correct development of the follicular epithelium, may cooperate with the genes egghead and notch to mediate germline-follicle cell adhesion. Brainiac mutant females and their offspring have multiple defects including ventralization of the eggshell, gaps in the follicular epithelium, and multiple layers of follicle cells around oocytes. The described overproliferation of follicle cells is similar to adenoma tumors. Brainiac females lay fewer eggs than wild-type flies, an occurrence likely due to destruction of mutant egg chambers within the mother. The embryos produced have a cancer-like neurogenic phenotype due to the conversion of epidermal cells to neuroblasts, resulting in excess nervous tissue. The brainiac gene, present on the X chromosome, encodes a 325 to amino acid protein with a putative signal sequence. The brainiac gene is expressed constitutively in the germline during the first 12 hours of embryogenesis. (Morisato and Anderson, supra; Goode, S. et al. (1992) Development 116:177–192; Goode, S. et al. (1996) Developmental Biol. 178:35–50; and Goode, S. et al. (1996) Development, supra.)

Recent work suggests that brainiac protein is a $\beta 1,3$-galactosyltransferase. (Yuan, Y. P. et al. (1997) Cell 88:9–11; and Hennet, T. et al. (1998) J. Biol. Chem. 273:58–65.) Galactosyltransferases are enzymes that transfer galactose to N-acetylglucosamine (GlcNAc)-terminating oligosaccharide chains that are part of glycoproteins or glycolipids or are free in solution. (Kolbinger, F. et al. (1998) J. Biol. Chem. 273:433–440.) $\beta 1,3$-galactosyltransferases form Type I carbohydrate chains with Gal ($\beta 1$-3)GlcNAc linkages. Known human and mouse $\beta 1,3$-galactosyltransferases appear to have a short cytosolic domain, a single transmembrane domain, and a catalytic domain with eight conserved regions. (Kolbinger, supra; and Hennet, supra.) In mouse UDP-galactose:$\beta$-N-acetylglucosamine $\beta 1,3$-galactosyltransferase-I region 1 is located at amino acid residues 78–83, region 2 is located at amino acid residues 93–102, region 3 is located at amino acid residues 116–119, region 4 is located at amino acid residues 147–158, region 5 is located at amino acid residues 172–183, region 6 is located at amino acid residues 203–206, region 7 is located at amino acid residues 236–246, and region 8 is located at amino acid residues 264–275. (Hennet, supra.) A variant of a sequence found within mouse UDP-galactose:$\beta$-N-acetylglucosamine $\beta 1,3$-galactosyltransferase-I region 8 is also found in bacterial galactosyltransferases, suggesting that this sequence defines a galactosyltransferase sequence motif. (Hennet, supra.) $\beta 1,4$-galactosyltransferases, which form Type II carbohydrate chains with Gal ($\beta 1$-4)GlcNAc linkages, are localized to both the Golgi and the cell surface. These enzymes have a short cytosolic domain, a transmembrane domain, and stem and catalytic domains which face the Golgi lumen or cell surface. A soluble $\beta 1,4$-galactosyltransferase is formed by cleaving the membrane-bound form. Amino acids conserved among $\beta 1,4$-galactosyltransferases include two disulfide-bonded cysteines and a putative UDP-galactose-binding site in the catalytic domain. (Yadav, S. and Brew, K. (1990) J. Biol. Chem. 265:14163–14169; Yadav, S. P. and Brew, K. (1991) J. Biol. Chem. 266:698–703; and Shaper, N. L. et al. (1997) J. Biol. Chem. 272:31389–31399.) $\beta 1,4$-galactosyltransferases have several specialized roles in addition to synthesizing carbohydrate chains on glycoproteins or glycolipids. In mammals, a $\beta 1,4$-galactosyltransferase, as part of a heterodimer with $\alpha$-lactalbumin, functions in lactating mammary gland lactose production. A $\beta 1,4$-galactosyltransferase on the surface of sperm functions as a receptor that specifically recognizes the egg. Cell surface $\beta 1,4$-galactosyltransferases also function in cell adhesion, cell/basal lamina interaction, and normal and metastatic cell migration. (Shur, B. D. (1993) Curr. Opin. Cell Biol. 5:854–863; and Shaper, supra.) An aberrantly cleaved soluble $\beta 1,4$-galactosyltransferase is secreted by a human ovarian cancer cell line. (Uejima, T. et al. (1992) Cancer Res. 52:6158–6163.)

Galactosyltransferases are part of a larger class of enzymes, the glycosyltransferases, which are implicated in the regulation of cellular growth, development, and differentiation. Many glycosyltransferases are localized to the Golgi while others are present on the cell surface and as soluble extracellular proteins. Cell surface membrane-bound glycosyltransferases may function in cell adhesion by binding carbohydrate substrates on adjacent cell surfaces or in the extracellular matrix. Secreted glycosyltransferases, derived in some cases from proteolytic cleavage of membrane-bound forms, may trigger cell surface receptors by binding their bound carbohydrates or may modify carbohydrates on cell surface molecules in a regulated fashion.

Extracellular carbohydrate moieties are developmentally regulated and may be involved in the regulation of cell migration. (Yuan, supra; Shur, supra; and Paulson, J. C. and Colley, K. J. (1989) J. Biol. Chem. 264:17615–17618.) Glycosyltransferases may be involved in autoimmune/ inflammatory disorders as many humans with autoimmune thyroid disorders have high levels of circulating antibodies directed against the enzymatic product of α1,3galactosyltransferase. (Etienne-Decerf, J. et al. (1987) Acta Endocrinol. 115:67–74.)

The discovery of new human galactosyltransferases and the polynucleotides encoding them satisfies a need in the art by providing new compositions useful in the diagnosis, treatment, and prevention of cancer, developmental disorders, reproductive disorders, and autoimmune/ inflammatory disorders.

SUMMARY OF THE INVENTION

The invention features substantially purified polypeptides, human galactosyltransferases, referred to collectively as "HUGA" and individually as "HUGA-1" and "HUGA-2." In one aspect, the invention provides a substantially purified polypeptide comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant having at least 90% amino acid identity to the amino acid sequences of SEQ ID NO:1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide having a sequence which is complementary to the polynucleotide comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:3, a fragment of SEQ ID NO:1, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:3, a fragment of SEQ ID NO:1, and a fragment of SEQ ID NO:3, as well as a purified agonist and a purified antagonist to the polypeptide. The invention also provides a method for treating or preventing a cancer, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a developmental disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a reproductive disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an autoimmune/inflammatory disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for detecting a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of HUGA-1.

FIGS. 2A, 2B, 2C, 2D, 2E, 2F, and 2G show the amino acid sequence (SEQ ID NO:3) and nucleic acid sequence (SEQ ID NO:4) of HUGA-2. The alignments were produced using MacDNASIS PRO™ software (Hitachi Software Engineering Co. Ltd., San Bruno, Calif.).

FIGS. 3A, 3B, and 3C show the amino acid sequence alignments among HUGA-1 (Incyte Clone number 1705085; SEQ ID NO:1), *Drosophila melanogaster* brainiac (GI 1150971; SEQ ID NO:5), and mouse UDP-galactose:β-N-acetylglucosamine β1,3-galactosyltransferase-I (GI 2745735; SEQ ID NO:6).

FIGS. 4A and 4B show the amino acid sequence alignment between HUGA-2 (Incyte Clone number 2551161; SEQ ID NO:3) and chicken β-1,4-galactosyltransferase (GI 1469908; SEQ ID NO:7). The alignments were produced using the multisequence alignment program of LASER-GENE™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HUGA," as used herein, refers to the amino acid sequences of substantially purified HUGA obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HUGA, increases or prolongs the duration of the effect of HUGA. Agonists may include proteins, nucleic acids, carbohydrates, or any other molecules which bind to and modulate the effect of HUGA.

An "allele" or an "allelic sequence," as these terms are used herein, is an alternative form of the gene encoding HUGA. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HUGA, as described herein, include those sequences with deletions, insertions, or substitutions of different nucleotides, resulting in a polynucleotide the same HUGA or a polypeptide with at least one functional characteristic of HUGA. Included within this definition are polymorphisms which may or may not be readily detectable using a particular oligonucleotide probe of the polynucleotide encoding HUGA, and improper or unexpected hybridization to alleles, with a locus other than the normal chromosomal locus for the polynucleotide sequence encoding HUGA. The encoded protein may also be "altered," and may contain deletions, insertions, or substitutions of amino acid residues which produce a silent change and result in a functionally equivalent HUGA. Deliberate amino acid substitutions may be made on the basis of similarity in polarity, charge, solubility, hydrophobicity, hydrophilicity, and/or the amphipathic nature of the residues, as long as the biological or immunological activity of HUGA is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HUGA which are preferably about 5 to about 15 amino acids in length and which retain some biological activity or immunological activity of HUGA. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to HUGA, decreases the amount or the duration of the effect of the biological or immunological activity of HUGA. Antagonists may include proteins, nucleic acids, carbohydrates, antibodies, or any other molecules which decrease the effect of HUGA.

As used herein, the term "antibody" refers to intact molecules as well as to fragments thereof, such as Fa, $F(ab')_2$, and Fv fragments, which are capable of binding the epitopic determinant. Antibodies that bind HUGA polypeptides.can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HUGA, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HUGA or fragments of HUGA may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HUGA, by northern analysis is indicative of the presence of nucleic acids encoding HUGA in a sample, and thereby correlates with expression of the transcript from the polynucleotide encoding HUGA.

A "deletion," as the term is used herein, refers to a change in the amino acid or nucleotide sequence that results in the absence of one or more amino acid residues or nucleotides.

The term "derivative," as used herein, refers to the chemical modification of HUGA, of a polynucleotide sequence encoding HUGA, or of a polynucleotide sequence complementary to a polynucleotide sequence encoding HUGA. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element", as used herein, in a microarray context, refer to hybridizable polynucleotides arranged on the surface of a substrate.

The term "modulate," as it appears herein, refers to a change in the activity of HUGA. For example, modulation may cause an increase or a decrease in protein activity, binding characteristics, or any other biological, functional, or immunological properties of HUGA.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.) The term "sample," as used herein, is used in its broadest sense. A biological sample suspected of containing nucleic acids encoding HUGA, or fragments thereof, or HUGA itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HUGA, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The Invention

The invention is based on the discovery of new human galactosyltransferases (HUGA), the polynucleotides encoding HUGA, and the use of these compositions for the diagnosis, treatment, and prevention of cancer, developmental disorders, reproductive disorders, and autoimmune/inflammatory disorders.

Nucleic acids encoding the HUGA-1 of the present invention were first identified in Incyte Clone 1705085 from the duodenal cDNA library (DUODNOT02) using a computer search for amino acid sequence alignments. A consensus sequence, SEQ ID NO:2, was derived from the following overlapping and/or extended nucleic acid sequences: Incyte Clones 861082 (BRAITUT03), 1705085 (DUODNOT02), 1798520 (COLNNOT27), and 3149055 (ADRENON04).

Figure 3B:
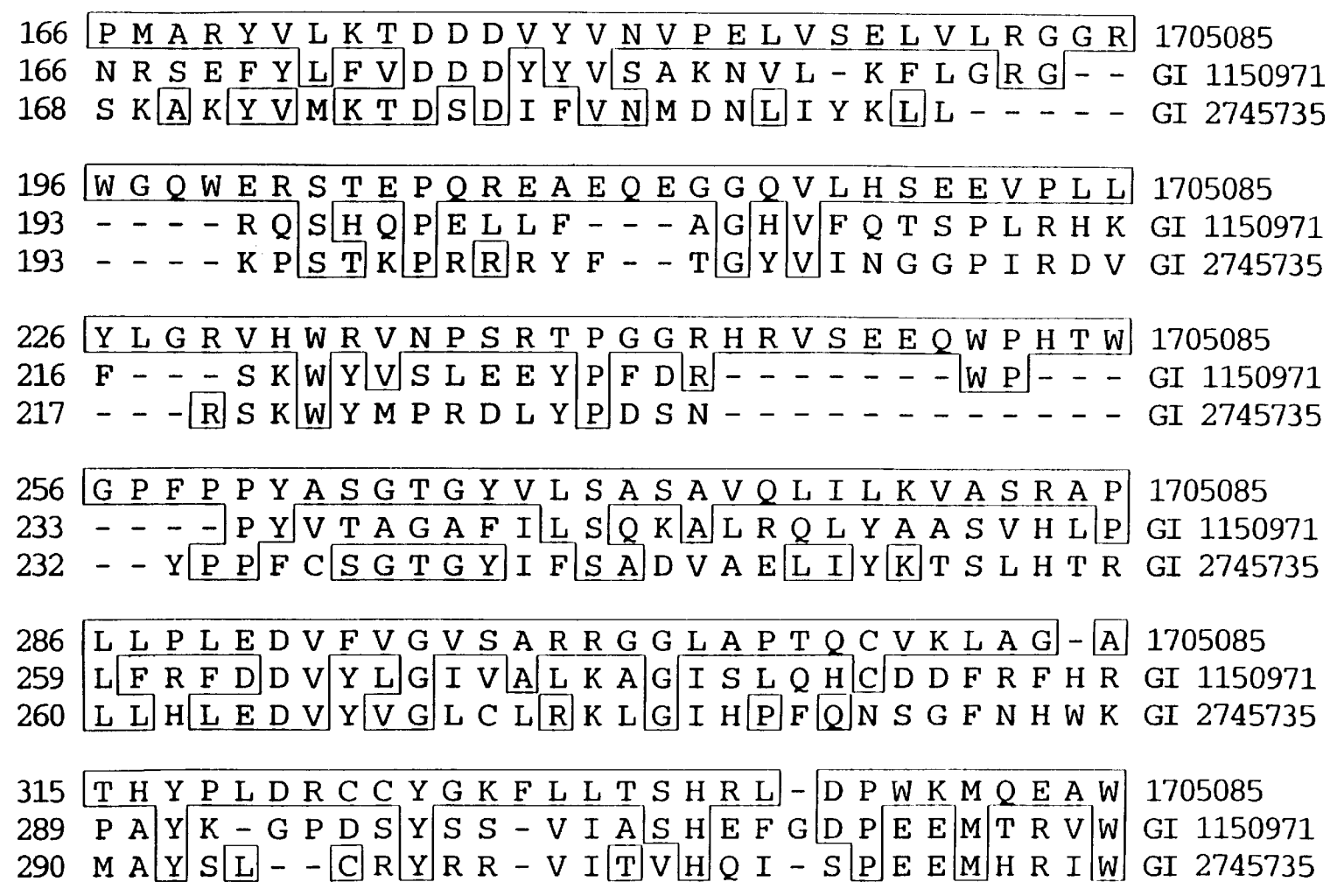
Figure 3C:
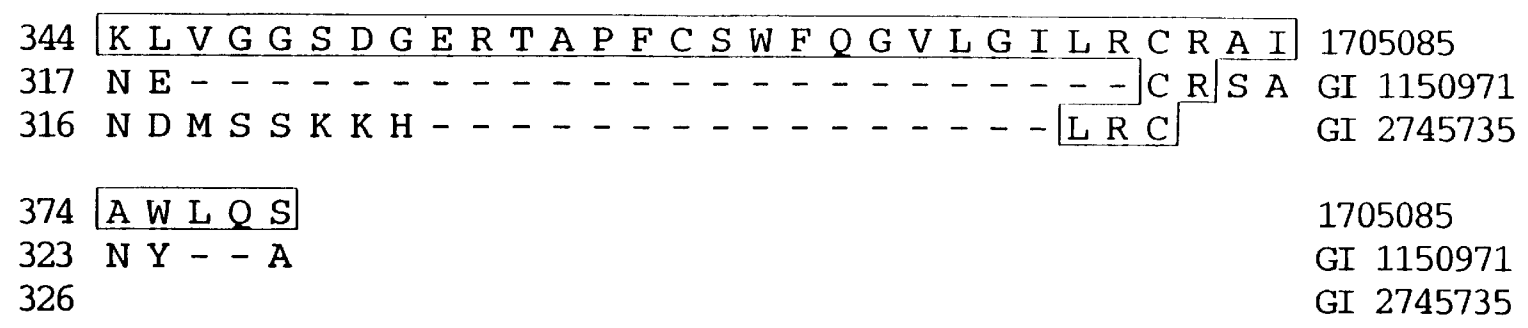

In one embodiment, the invention encompasses a polypeptide comprising the amino acid sequence of SEQ ID NO:1, as shown in FIGS. 1A, 1B, 1C, and 1D. HUGA-1 is 378 amino acids in length and has a potential signal sequence from M1 to about T21. HUGA-1 has a potential N-glycosylation site at residue N149; three potential casein kinase II phosphorylation sites at residues T79, T174, and S349; four potential protein kinase C phosphorylation sites at residues S146, T151, S297, and S331; and one potential tyrosine kinase phosphorylation site at Y179. As shown in FIGS. 3A, 3B, and 3C, HUGA-1 has chemical and structural homology with *Drosophila melanogaster* brainiac (GI 1150971; SEQ ID NO:5) and mouse UDP-galactose: β-N-acetylglucosamine β1,3-galactosyltransferase-I (GI 2745735; SEQ ID NO:6). In particular, HUGA-1 shares 23% identity with *Drosophila melanogaster* brainiac and 24% identity with mouse UDP-galactose: β-N-acetylglucosamine β1,3-galactosyltransferase-I. HUGA-1 shows high homology to seven of the eight conserved regions of mouse β1,3-galactosyltransferases. HUGA-1 amino acid residues 71–76 are 83% identical to mouse UDP-galactose: β-N-acetylglucosamine β1,3-galactosyltransferase-I region 1; HUGA-1 amino acid residues 86–95 are 60% identical to mouse UDP-galactose: β-N-acetylglucosamine β1,3-galactosyltransferase-I region 2; HUGA-1 amino acid residues 109–112 are 100% identical to mouse UDP-galactose: β-N-acetylglucosamine β1,3-galactosyltransferase-I region 3; HUGA-1 amino acid residues 145–156 are 83% identical to mouse UDP-galactose: β-N-acetylglucosamine β1,3-galactosyltransferase-I region 4; HUGA-1 amino acid residues 170–181 are 67% identical to mouse UDP-galactose: β-N-acetylglucosamine β1,3-galactosyltransferase-I region 5; HUGA-1 amino acid residues 262–272 are 64% identical to mouse UDP-galactose: β-N-acetylglucosamine p 1,3-galactosyltransferase-I region 7; and HUGA-1 amino acid residues 290–301 are 50% identical to mouse UDP-galactose: β-N-acetylglucosamine β1,3-galactosyltransferase-I region 8. HUGA-1 has a potential galactosyltransferase motif at E290DVFVG. A fragment of SEQ ID NO:2 from about nucleotide 130 to about nucleotide 156 is useful for hybridization. Northern analysis shows the expression of this sequence in various libraries, at least 36% of which are immortalized or cancerous and at least 57% of which involve immune response. Of particular note is the expression of HUGA-1 in endocrine, gastrointestinal, hematopoietic/immune, nervous, and female reproductive tissues.

Nucleic acids encoding the HUGA-2 of the present invention were first identified in Incyte Clone 2551161 from the lung tumor cDNA library (LUNGTUT06) using a computer search for amino acid sequence alignments. A consensus sequence, SEQ ID NO:4, was derived from the following overlapping and/or extended nucleic acid sequences: Incyte Clones 094232 (PITUNOT01), 514851 (MMLR1DT01), 1727376 (PROSNOT14), 1804115 (SINTNOT13), 1856849 (PROSNOT18), 2478323 (SMCANOT01), 2529537 (GBLANOT02), 2551161 (LUNGTUT06), and 3176331 (UTRSTUT04).

In one embodiment, the invention encompasses a polypeptide comprising the amino acid sequence of SEQ ID NO:3, as shown in FIGS. 2A, 2B, 2C, 2D, 2E, 2F, and 2G. HUGA-2 is 344 amino acids in length and has a potential cytosolic domain from M1 to about R14, a potential transmembrane region from about L15 to about S31, a potential stem domain from about N32 to about N76, and a potential catalytic domain from about C77 to A344. HUGA-2 has three potential N-glycosylation sites at residues N4, N220, and N335; one potential casein kinase II phosphorylation site at residue T97; four potential protein kinase C phosphorylation sites at residues S10, S68, T69, and S321; and two potential tyrosine kinase phosphorylation sites at Y158 and Y284. As shown in FIGS. 4A and 4B, HUGA-2 has chemical and structural homology with chicken β-1,4-galactosyltransferase CK-I (GI 1469908; SEQ ID NO:7). In particular, HUGA-2 shares 43% identity with chicken β-1,4-galactosyltransferase CK-I. The potential catalytic domain of HUGA-2 is 52% identical to that of chicken β1,4-galactosyltransferase CK-I. The two cysteine residues of chicken β1,4-galactosyltransferase CK-I that are proposed to form a disulfide bond are conserved in HUGA-2 at C77 and C189. HUGA-2 contains a potential galactosyltransferase UDP-galactose binding motif at K283YTMVFHTRDK. A fragment of SEQ ID NO:4 from about nucleotide 432 to about nucleotide 455 is useful for hybridization. Northern analysis shows the expression of this sequence in various libraries, at least 53% of which are immortalized or cancerous and at least 31% of which involve immune response. Of particular note is the expression of HUGA-2 in female reproductive, male reproductive, gastrointestinal, hematopoietic/immune, fetal, and nervous tissues.

The invention also encompasses HUGA variants. A preferred HUGA variant is one which has at least about 80%, more preferably at least about 90%, and most preferably at least about 95% amino acid sequence identity to the HUGA amino acid sequence, and which contains at least one functional or structural characteristic of HUGA.

The invention also encompasses polynucleotides which encode HUGA. In a particular embodiment, the invention encompasses a polynucleotide sequence comprising the sequence of SEQ ID NO:2, as shown in FIGS. 1A, 1B, 1C, and 1D, which encodes a HUGA-1. In a further embodiment, the invention encompasses the polynucleotide sequence comprising the sequence of SEQ ID NO:4, as shown in FIGS. 2A, 2B, 2C, 2D, 2E, 2F, and 2G, which encodes a HUGA-2.

The invention also encompasses a variant of a polynucleotide sequence encoding HUGA. In particular, such a variant polynucleotide sequence will have at least about 80%, more preferably at least about 90%, and most preferably at least about 95% polynucleotide sequence identity to the polynucleotide sequence encoding HUGA. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of HUGA.

It will be appreciated by those skilled in the art that as a result of the degeneracy of the genetic code, a multitude of polynucleotide sequences encoding HUGA, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HUGA, and all such variations are to be considered as being specifically disclosed.

Although nucleotide sequences which encode HUGA and its variants are preferably capable of hybridizing to the nucleotide sequence of the naturally occurring HUGA under appropriately selected conditions of stringency, it may be advantageous to produce nucleotide sequences encoding HUGA or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUGA and its derivatives without altering the encoded amino acid sequences include the production of RNA transcripts having more desirable properties, such as a greater half-life, than transcripts produced from the naturally occurring sequence.

The invention also encompasses production of DNA sequences which encode HUGA and HUGA derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HUGA or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4, under various conditions of stringency. (See, e.g., Wahl, G. M. and S. L. Berger (1987) Methods Enzymol. 152:399–407; Kimmel, A. R. (1987) Methods Enzymol. 152:507–511.) Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HUGA may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO 4.06™ Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 720° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output light intensity may be converted to electrical signal using appropriate software (e.g., Genotyper™ and Sequence Navigators™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HUGA may be cloned in recombinant DNA molecules that direct expression of HUGA, or fragments or functional equivalents thereof, in appropriate host cells. Due to the inherent degeneracy of the genetic code, other DNA sequences which encode substantially the same or a functionally equivalent amino acid sequence may be produced and used to express HUGA.

The nucleotide sequences of the present invention can be engineered using methods generally known in the art in order to alter HUGA-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HUGA may be synthesized, in whole or in part, using chemical methods well known in the art. (See, e.g., Caruthers, M. H. et al. (1980) Nucl. Acids Symp. Ser. (7)215–223, and Horn, T. et al. (1980) Nucl. Acids Symp. Ser. (7)225–232.) Alternatively, HUGA itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of HUGA, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392421.) The composition of the synthetic peptides may be confirmed by amino acid analysis or by sequencing. (See, e.g., Creighton, T. (1984) *Proteins. Structures and Molecular Properties*, W H Freeman and Co., New York, N.Y.)

In order to express a biologically active HUGA, the nucleotide sequences encoding HUGA or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HUGA. Such elements may vary in their strength and specificity. Specific initiation signals may also be used to achieve more efficient translation of sequences encoding HUGA. Such signals include the ATG initiation codon and adjacent sequences, e.g. the Kozak sequence. In cases where sequences encoding HUGA and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HUGA and appropriate transcriptional and translational control elements. These methods include in vitro recombinant DNA techniques, synthetic techniques, and in vivo genetic recombination. (See, e.g., Sambrook, J.

et al. (1989) *Molecular Cloning. A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding HUGA. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HUGA. For example, routine cloning, subcloning, and propagation of polynucleotide sequences encoding HUGA can be achieved using a multifunctional *E. coli* vector such as Bluescript® (Stratagene) or pSport1™ plasmid (GIBCO BRL). Ligation of sequences encoding HUGA into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HUGA are needed, e.g. for the production of antibodies, vectors which direct high level expression of HUGA may be used. For example, vectors containing the strong, inducible T5 or T7 bacteriophage promoter may be used.

Yeast expression systems may be used for production of HUGA. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of HUGA. Transcription of sequences encoding HUGA may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding HUGA may be ligated into an adenovirus transcription/translation complex consisting of the late promoter and tripartite leader sequence. Insertion in a non-essential E1 or E3 region of the viral genome may be used to obtain infective virus which expresses HUGA in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of HUGA in cell lines is preferred. For example, sequences encoding HUGA can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate GUS, luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HUGA is inserted within a marker gene sequence, transformed cells containing sequences encoding HUGA can be identified by the absence of marker gene function. Alternatively, a marker gene can be placed in tandem with a sequence encoding HUGA under the control of a single promoter. Expression of the marker gene in response to induction or selection usually indicates expression of the tandem gene as well.

In general, host cells that contain the nucleic acid sequence encoding HUGA and that express HUGA may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HUGA using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HUGA is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUGA include oligolabeling, nick translation, end-labeling, or PCR amplification using a labeled nucleotide. Alternatively, the sequences encoding HUGA, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HUGA may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HUGA may be designed to contain signal sequences which direct secretion of HUGA through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding HUGA may be ligated to a heterologous sequence resulting in translation of a fusion protein in any of the aforementioned host systems. For example, a chimeric HUGA protein containing a heterologous moiety that can be recognized by a commercially available antibody may facilitate the screening of peptide libraries for inhibitors of HUGA activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HUGA encoding sequence and the heterologous protein sequence, so that HUGA may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled HUGA may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HUGA may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of HUGA may be synthesized separately and then combined to produce the full length molecule.

Therapeutics

Chemical and structural homology exists among HUGA-1 and brainiac from *Drosophila melanogaster* (GI 150971) and UDP-galactose: β-N-acetylglucosamine β1,3-galactosyltransferase-I from mouse (GI 2745735). In addition, HUGA-1 is expressed in libraries derived from cancerous, inflamed, hematopoietic/immune, and female reproductive tissues.

Chemical and structural homology exists between HUGA-2 and β-1,4-galactosyltransferase CK-I from chicken (GI 1469908). In addition, HUGA-2 is expressed in cancerous, inflamed, hematopoietic/immune, fetal, female reproductive, and male reproductive tissues.

Therefore, HUGA appears to play a role in cancer, developmental disorders, reproductive disorders, and autoimmune/inflammatory disorders.

Therefore, in one embodiment, HUGA or a fragment or derivative thereof may be administered to a subject to treat or prevent a cancer. Such cancers can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HUGA or a fragment or derivative thereof may be administered to a subject to treat or prevent a cancer including, but not limited to, those described above.

In a further embodiment, a pharmaceutical composition comprising a substantially purified HUGA in conjunction with a suitable pharmaceutical carrier may be administered to a subject to treat or prevent a cancer including, but not limited to, those provided above.

In still another embodiment, an agonist which modulates the activity of HUGA may be administered to a subject to treat or prevent a cancer including, but not limited to, those listed above.

In another embodiment, HUGA or a fragment or derivative thereof may be administered to a subject to treat or prevent a developmental disorder. Such developmental disorders can include, but are not limited to, renal tubular acidosis, anemia, Cushing's syndrome, achondroplastic dwarfism, Duchenne and Becker muscular dystrophy, epilepsy, gonadal dysgenesis, Wilms' tumor, aniridia, genital anomalies, and mental retardation (WAGR) syndrome, Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma; cataract, and sensorineural hearing loss.

In another embodiment, a vector capable of expressing HUGA or a fragment or derivative thereof may be administered to a subject to treat or prevent a developmental disorder including, but not limited to, those described above.

In a further embodiment, a pharmaceutical composition comprising a substantially purified HUGA in conjunction with a suitable pharmaceutical carrier may be administered to a subject to treat or prevent a developmental disorder including, but not limited to, those provided above.

In still another embodiment, an agonist which modulates the activity of HUGA may be administered to a subject to treat or prevent a developmental disorder including, but not limited to, those listed above.

In another embodiment, HUGA or a fragment or derivative thereof may be administered to a subject to treat or prevent a reproductive disorder. Such reproductive disorders can include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia.

In another embodiment, a vector capable of expressing HUGA or a fragment or derivative thereof may be administered to a subject to treat or prevent a reproductive disorder including, but not limited to, those described above.

In a further embodiment, a pharmaceutical composition comprising a substantially purified HUGA in conjunction with a suitable pharmaceutical carrier may be administered to a subject to treat or prevent a reproductive disorder including, but not limited to, those provided above.

In still another embodiment, an agonist which modulates the activity of HUGA may be administered to a subject to treat or prevent a reproductive disorder including, but not limited to, those listed above.

In a further embodiment, an antagonist of HUGA may be administered to a subject to treat or prevent an autoimmune/inflammatory disorder. Such an autoimmune/inflammatory disorder may include, but is not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, complications of cancer, hemodialysis, and extracorporeal circulation, viral, bacterial, fungal, parasitic, protozoal, and helminthic infections, and trauma. In one aspect, an antibody which specifically binds HUGA may be used directly as an antagonist or indirectly as a targeting or delivery mechanism for bringing a pharmaceutical agent to cells or tissue which express HUGA.

In an additional embodiment, a vector expressing the complement of the polynucleotide encoding HUGA may be administered to a subject to treat or prevent an autoimmune/inflammatory disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUGA may be produced using methods which are generally known in the art. In particular, purified HUGA may be used to produce antibodies or to screen libraries of pharmaceutical agents to identify those which specifically bind HUGA. Antibodies to HUGA may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HUGA or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUGA have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HUGA amino acids may be fused with those of another protein, such as KLH, and antibodies to the chimeric molecule may be produced.

Monoclonal antibodies to HUGA may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495497; Kozbor, D. et al. (1985) J. Immunol. Methods 81:3142; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of."chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HUGA-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.) Antibody fragments which contain specific binding sites for HUGA may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUGA and its specific antibody. A two-site, monoclonal-based immunoassay utilizing monoclonal antibodies reactive to two non-interfering HUGA epitopes is preferred, but a competitive binding assay may also be employed. (Maddox, supra.)

In another embodiment of the invention, the polynucleotides encoding HUGA, or any fragment or complement thereof, may be used for therapeutic purposes. In one aspect, the complement of the polynucleotide encoding HUGA may be used in situations in which it would be desirable to block the transcription of the mRNA. In particular, cells may be transformed with sequences complementary to polynucleotides encoding HUGA. Thus, complementary molecules or fragments may be used to modulate HUGA activity, or to achieve regulation of gene function. Such technology is now well known in the art, and sense or antisense oligonucleotides or larger fragments can be designed from various locations along the coding or control regions of sequences encoding HUGA.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding HUGA. (See, e.g., Sambrook, supra; and Ausubel, supra.)

Genes encoding HUGA can be turned off by transforming a cell or tissue with expression vectors which express high levels of a polynucleotide, or fragment thereof, encoding HUGA. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HUGA. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HUGA.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUGA. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HUGA, antibodies to HUGA, and mimetics, agonists, antagonists, or inhibitors of HUGA. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration m ay be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following:1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HUGA, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HUGA or fragments thereof, antibodies of HUGA, and agonists, antagonists or inhibitors of HUGA, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population)or $LD_{50}$. (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUGA may be used for the diagnosis of disorders characterized by expression of HUGA, or in assays to monitor patients being treated with HUGA or agonists, antagonists, or inhibitors of HUGA. Antibodies useful for diagnostic purposes may be prepared in the same manner as described above for therapeutics. Diagnostic assays for HUGA include methods which utilize the antibody and a label to detect HUGA in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HUGA, including ELISAs, RIAs, and FACS, are known in the art and provide a basis for diagnosing altered or abnormal levels of HUGA expression. Normal or standard values for HUGA expression are established by combining body fluids or cell extracts taken from normal mammalian subjects, preferably human, with antibody to HUGA under conditions suitable for complex formation. The amount of standard complex formation may be quantitated by various methods, preferably by photometric means. Quantities of HUGA expressed in subject, control, and disease samples from biopsied tissues are compared with the standard values. Deviation between standard and subject values establishes the parameters for diagnosing disease.

In another embodiment of the invention, the polynucleotides encoding HUGA may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUGA may be correlated with disease. The diagnostic assay may be used to determine absence, presence, and excess expression of HUGA, and to monitor regulation of HUGA levels during therapeutic intervention.

In one aspect, hybridization with PCR probes which are capable of detecting polynucleotide sequences, including genomic sequences, encoding HUGA or closely related molecules may be used to identify nucleic acid sequences which encode HUGA. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HUGA, alleles, or related sequences.

Probes may also be used for the detection of related sequences, and should preferably have at least 50% sequence identity to any of the HUGA encoding sequences. The hybridization probes of the subject invention may be DNA or RNA and may be derived from the sequences of SEQ ID NO:2 and SEQ ID NO:4 or from genomic sequences including promoters, enhancers, and introns of the HUGA gene.

Means for producing specific hybridization probes for DNAs encoding HUGA include the cloning of polynucleotide sequences encoding HUGA or HUGA derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HUGA may be used for the diagnosis of a disorder associated with expression of HUGA. Examples of such disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; developmental disorders such as renal tubular acidosis, anemia, Cushing's syndrome, achondroplastic dwarfism, Duchenne and Becker muscular dystrophy, epilepsy, gonadal dysgenesis, Wilms' tumor, aniridia, genital anomalies, and mental retardation (WAGR) syndrome, Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, and sensorineural hearing loss; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; and autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, complications of cancer, hemodialysis, and extracorporeal circulation, viral, bacterial, fungal, parasitic, protozoal, and helminthic infections, and trauma. The polynucleotide sequences encoding HUGA may be used in Southern or northern analysis, dot blot, or other membrane-based technologies; in PCR technologies; in dipstick, pin, and ELISA assays; and in microarrays utilizing fluids or tissues from patients to detect altered HUGA expression. Such qualitative or quantitative methods are well known in the art.

In a particular aspect, the nucleotide sequences encoding HUGA may be useful in assays that detect the presence of associated disorders, particularly those mentioned above. The nucleotide sequences encoding HUGA may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HUGA in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HUGA, a normal or standard profile for expression is established. This may be accomplished by combining body fluids or cell extracts taken from normal subjects, either animal or human, with a sequence, or a fragment thereof, encoding HUGA, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUGA may involve the use of PCR. These oligomers may be chemically synthesized, generated enzymatically, or produced in vitro. Oligomers will preferably contain a fragment of a polynucleotide encoding HUGA, or a fragment of a polynucleotide complementary to the polynucleotide encoding HUGA, and will be employed under optimized conditions for identification of a specific gene or condition. Oligomers may also be employed under less stringent conditions for detection or quantitation of closely related DNA or RNA sequences.

Methods which may also be used to quantitate the expression of HUGA include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding HUGA may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.) Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HUGA on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature. 336:577–580.) The nucleotide sequence of the subject invention may also be used to detect differences in the chromosomal location due to translocation, inversion, etc., among normal, carrier, or affected individuals.

In another embodiment of the invention, HUGA, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HUGA and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HUGA, or fragments thereof, and washed. Bound HUGA is then detected by methods well known in the art. Purified HUGA can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUGA specifically compete with a test compound for binding HUGA. In this manner, antibodies can be used to detect the presence of any peptide which shares one or more antigenic determinants with HUGA.

In additional embodiments, the nucleotide sequences which encode HUGA may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

DUODNOT02

The DUODNOT02 cDNA library was constructed from microscopically normal duodenum tissue obtained from an 8-year-old Caucasian female following death from a head trauma. The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNase-free water, and DNase treated at 37° C. RNA extraction and precipitation were repeated as before. The mRNA was isolated with the Qiagen Oligotex kit (QIAGEN, Inc., Chatsworth, Calif.) and used to construct the cDNA library.

The mRNA was handled according to the recommended protocols in SuperScript™, a plasmid system for cDNA synthesis and plasmid cloning (Cat. #18248-013, GIBCO BRL). The cDNAs were fractionated on a Sepharose CL4B column (Cat. #275105-01, Pharmacia), and those cDNAs exceeding 400 bp were ligated into pSport I. The plasmid pSport I was subsequently transformed into DH5α™ competent cells (Cat. #182584-012, GIBCO BRL).

LUNGTUT06

The LUNGTUT06 cDNA library was constructed from cancerous lung tissue obtained from an 80-year-old Caucasian female during a segmental lung resection following diagnosis of malignant neoplasms of the bronchus, lung and ovary. Pathology indicated a metastatic granulosa cell tumor forming a mass at the posterior and superior segment of the right lung. The frozen tissue was homogenized and lysed in TRIzol reagent (1 g tissue/10 ml TRIzol; Cat. #10296-028; GIBCO BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper layer was removed to a fresh tube and the RNA precipitated with isopropanol, resuspended in DEPC-treated water, and DNase treated for 25 minutes at 37° C. The RNA was re-extracted twice with acid phenol-chloroform pH 4.7 and precipitated using 0.3M sodium acetate and 2.5 volumes ethanol. The mRNA was isolated with the Qiagen Oligotex kit (QIAGEN, Inc., Chatsworth, Calif.) and used to construct the cDNA library.

The mRNA was handled according to the recommended protocols in SuperScript™, a plasmid system for cDNA synthesis and plasmid cloning (Cat. #18248-013, GIBCO BRL). The cDNAs were fractionated on a Sepharose CL4B column (Cat. #275105-01; Pharmacia), and those cDNAs exceeding 400 bp were ligated into pINCY 1. The plasmid pINCY 1was subsequently transformed into DH5α™ competent cells (Cat. #18258-012; GIBCO BRL).

II. Isolation and Sequencing of cDNA Clones

Plasmid DNA was released from the cells and purified using the REAL Prep 96 plasmid kit (Catalog #26173, QIAGEN, Inc.). This kit enabled the simultaneous purification of 96 samples in a 96-well block using multi-channel reagent dispensers. The recommended protocol was employed except for the following changes:1) the bacteria were cultured in 1 ml of sterile Terrific Broth™ (Catalog #22711, GIBCO BRL), a bacterial growth medium, with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems, and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

% sequence identity x % maximum BLAST score/100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HUGA occurs. Abundance and percent abundance are also reported. Abundance directly reflects the number of times a particular transcript is represented in a cDNA library, and percent abundance is abundance divided by the total number of sequences examined in the cDNA library.

V. Extension of HUGA Encoding Polynucleotides

The nucleic acid sequences of Incyte Clones 1705085 and 2551161 were used to design oligonucleotide primers for extending partial nucleotide sequences to full length. For each nucleic acid sequence, one primer was synthesized to initiate extension of an antisense polynucleotide, and another was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent *E. coli* cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2x carb). The following day, several colonies were randomly picked from each plate and cultured in 150 µl of liquid LB/2x carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 µCi of [$\gamma$-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing 10' counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the HUGA-encoding sequences, or any parts thereof, are used to detect, decrease, or inhibit expression of naturally occurring HUGA. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HUGA. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUGA-encoding transcript.

IX. Expression of HUGA

Expression and purification of HUGA is achieved using bacterial or virus-based expression systems. For expression of HUGA in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HUGA upon induction with isopropyl beta-D-thiogalactopyranoside (IPTG). Expression of HUGA in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HUGA by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, HUGA is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from HUGA at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified HUGA obtained by these methods can be used directly in the following activity assay.

X. Demonstration of HUGA Activity

HUGA activity is determined by measuring the transfer of galactose from UDP-galactose to a GlcNAc-terminated oligosaccharide chain in a radioactive assay. (Kolbinger, supra.) The sample is incubated with 14 µl of assay stock solution (180 mM sodium cacodylate, pH 6.5, 1 mg/ml bovine serum albumin, 0.26 mM UDP-galactose, 2 µl of UDP-[$_3$H]galactose), 1 µl of MnCl$_2$ (500 mM), and 2.5 µl of GlcNAcβO-(CH$_2$)$_8$-CO$_2$Me (37 mg/ml in dimethyl sulfoxide) for 60 minutes at 37° C. The reaction is quenched by the addition of 1 ml of water and loaded on a C18 Sep-Pak cartridge (Waters), and the column is washed twice with 5 ml of water to remove unreacted UDP-[$^3$H]galactose. The [$^3$H]galactosylated GlcNAcβO-(CH$_2$)$_8$-CO$_2$Me remains bound to the column during the water washes and is eluted with 5 ml of methanol. Radioactivity in the eluted material is measured by liquid scintillation counting and is proportional to HUGA activity in the starting sample.

XI. Functional Assays

HUGA function is assessed by expressing the sequences encoding HUGA at physiologically elevated levels in mammalian cell culture systems. cDNA is subcloned into a mammalian expression vector containing a strong promoter that drives high levels of cDNA expression. Vectors of choice include pCMV.Sport™ (Life Technologies™, Gaithersburg, Md.) and pCR™ 3.1 (Invitrogen™, Carlsbad, Calif., both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP and to evaluate properties such as their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of HUGA on gene expression can be assessed using highly purified populations of cells transfected with sequences encoding HUGA and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding HUGA and other genes of interest can be analyzed by Northern analysis or microarray techniques.

XII. Production of HUGA Specific Antibodies

HUGA substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the HUGA amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XIII. Purification of Naturally Occurring HUGA Using Specific Antibodies

Naturally occurring or recombinant HUGA is substantially purified by immunoaffinity chromatography using antibodies specific for HUGA. An immunoaffinity column is constructed by covalently coupling anti-HUGA antibody to an activated chromatographic resin, such as CNBr-activated Sepharose (Pharmacia & Upjohn). After the coupling, the resin is blocked and washed according to the manufacturer's instructions.

Media containing HUGA are passed over the immunoaffinity column, and the column is washed under conditions that allow the preferential absorbance of HUGA (e.g., high ionic strength buffers in the presence of detergent). The column is eluted under conditions that disrupt antibody/HUGA binding (e.g., a buffer of pH 2 to pH 3, or a high concentration of a chaotrope, such as urea or thiocyanate ion), and HUGA is collected.

XIV. Identification of Molecules Which Interact with HUGA

HUGA, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HUGA, washed, and any wells with labeled HUGA complex are assayed. Data obtained using different concentrations of HUGA are used to calculate values for the number, affinity, and association of HUGA with the candidate molecules.

Various modifications and variations of the described methods and systems of the invention will be apparent to those skilled in the art without departing from the scope and spirit of the invention. Although the invention has been described in connection-with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising the amino acid sequence of SEQ ID NO:3.

2. A purified polypeptide having at least 90% amino acid sequence identity to the amino acid sequence of claim 1, and which retains galactosyltransferase activity.

3. A composition comprising the polypeptide of claim 1 in conjunction with a suitable carrier.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 378 amino acids
      (B) TYPE: amino acid
      (C) STRANDEDNESS: single
      (D) TOPOLOGY: linear (vii) IMMEDIATE SOURCE:
      (A) LIBRARY: DUODNOT02
      (B) CLONE: 1705085

(xi) SEQUENCE DESCRIPTION: SEQ ID NO: 1:

```
Met Gln Leu Arg Leu Phe Arg Arg Leu Leu Leu Ala Ala Leu Leu Leu
  1               5                  10                  15

Val Ile Val Trp Thr Leu Phe Gly Pro Ser Gly Leu Gly Glu Glu Leu
             20                  25                  30

Leu Ser Leu Ser Leu Ala Ser Leu Leu Pro Ala Pro Ala Ser Pro Gly
         35                  40                  45

Pro Pro Leu Ala Leu Pro Arg Leu Leu Ile Pro Asn Gln Glu Ala Cys
     50                  55                  60

Ser Gly Pro Gly Ala Pro Pro Phe Leu Leu Ile Leu Val Cys Thr Ala
 65                  70                  75                  80

Pro Glu Asn Leu Asn Gln Arg Asn Ala Ile Arg Ala Ser Trp Gly Gly
                 85                  90                  95

Leu Arg Glu Ala Arg Gly Leu Arg Val Gln Thr Leu Phe Leu Leu Gly
                100                 105                 110

Glu Pro Asn Ala Gln His Pro Val Trp Gly Ser Gln Gly Ser Asp Leu
            115                 120                 125

Ala Ser Glu Ser Ala Ala Gln Gly Asp Ile Leu Gln Ala Ala Phe Gln
        130                 135                 140

Asp Ser Tyr Arg Asn Leu Thr Leu Lys Thr Leu Ser Gly Leu Asn Trp
145                 150                 155                 160

Ala Glu Lys His Cys Pro Met Ala Arg Tyr Val Leu Lys Thr Asp Asp
                165                 170                 175

Asp Val Tyr Val Asn Val Pro Glu Leu Val Ser Glu Leu Val Leu Arg
            180                 185                 190

Gly Gly Arg Trp Gly Gln Trp Glu Arg Ser Thr Glu Pro Gln Arg Glu
        195                 200                 205

Ala Glu Gln Glu Gly Gly Gln Val Leu His Ser Glu Glu Val Pro Leu
    210                 215                 220

Leu Tyr Leu Gly Arg Val His Trp Arg Val Asn Pro Ser Arg Thr Pro
225                 230                 235                 240

Gly Gly Arg His Arg Val Ser Glu Glu Gln Trp Pro His Thr Trp Gly
                245                 250                 255

Pro Phe Pro Pro Tyr Ala Ser Gly Thr Gly Tyr Val Leu Ser Ala Ser
            260                 265                 270

Ala Val Gln Leu Ile Leu Lys Val Ala Ser Arg Ala Pro Leu Leu Pro
        275                 280                 285

Leu Glu Asp Val Phe Val Gly Val Ser Ala Arg Arg Gly Gly Leu Ala
    290                 295                 300
```

```
Pro Thr Gln Cys Val Lys Leu Ala Gly Ala Thr His Tyr Pro Leu Asp
305                 310                 315                 320

Arg Cys Cys Tyr Gly Lys Phe Leu Leu Thr Ser His Arg Leu Asp Pro
                325                 330                 335

Trp Lys Met Gln Glu Ala Trp Lys Leu Val Gly Gly Ser Asp Gly Glu
            340                 345                 350

Arg Thr Ala Pro Phe Cys Ser Trp Phe Gln Gly Val Leu Gly Ile Leu
        355                 360                 365

Arg Cys Arg Ala Ile Ala Trp Leu Gln Ser
    370                 375

(2) INFORMATION FOR SEQ ID NO: 2:

(i) SEQUENCE CHARACTERISTICS:
        (A) LENGTH: 1434 base pairs
        (B) TYPE: nucleic acid
        (C) STRANDEDNESS: single
        (D) TOPOLOGY: linear (vii) IMMEDIATE SOURCE:
        (A) LIBRARY: DUODNOT02
        (B) CLONE: 1705085

(xi) SEQUENCE DESCRIPTION: SEQ ID NO: 2:

CGGCTCGAGC TTACGGATCC CCTCGGAGTA CGCCGCACCA TGCAGCTCAG GCTCTTCCGG      60

CGCCTCCTTC TCGCCGCTTT GCTGCTGGTG ATCGTCTGGA CCCTCTTCGG GCCTTCGGGG     120

TTGGGGGAGG AGCTGCTGAG CCTCTCACTA GCCTCCCTGC TCCCAGCCCC CGCCTCACCG     180

GGGCCGCCCC TGGCCCTGCC CCGCCTCTTG ATCCCCAACC AGGAAGCTTG CAGTGGTCCC     240

GGGGCCCCTC CCTTCCTGCT CATCCTGGTG TGCACGGCTC CGGAGAACCT GAACCAGAGA     300

AACGCCATTC GGGCTTCGTG GGGCGGGCTG CGCGAGGCCC GGGGGCTCAG GGTACAGACG     360

CTATTCTTGC TGGGAGAGCC GAACGCACAG CACCCCGTGT GGGGTTCCCA GGGAGTGAC      420

CTGGCCTCGG AGTCAGCAGC CCAGGGGGAT ATCTTGCAGG CCGCCTTCCA GGACTCCTAC     480

CGCAACCTCA CCCTAAAGAC CCTCAGCGGG CTGAACTGGG CTGAGAAACA CTGCCCCATG     540

GCCCGATACG TCCTCAAGAC GGACGATGAT GTGTATGTCA ACGTCCCTGA ACTGGTATCA     600

GAGCTGGTCT TGCGAGGGGG CCGTTGGGGG CAATGGGAGA GAAGCACGGA ACCCCAGAGA     660

GAGGCTGAGC AGGAAGGAGG CCAGGTTTTG CACAGCGAGG AAGTGCCTCT TCTGTACTTG     720

GGCCGGGTGC ACTGGCGCGT GAACCCCTCT CGGACACCGG GGGCAGGCA  CCGCGTATCA     780

GAGGAGCAGT GGCCTCACAC CTGGGGCCCC TTTCCACCCT ATGCCTCAGG CACGGGGTAT     840

GTGCTGTCAG CGTCTGCTGT GCAGCTCATT CTCAAGGTGG CCAGCCGGGC ACCCCTTCTC     900

CCATTAGAGG ATGTCTTTGT GGGGGTAAGT GCCCGACGAG GAGGCCTCGC CCCAACACAG     960

TGTGTCAAGC TGGCTGGTGC CACCCACTAC CCGCTAGACC GGTGCTGCTA TGGGAAATTC    1020

CTGCTGACGT CCCACAGGCT GGACCCCTGG AAGATGCAGG AAGCCTGGAA GCTGGTGGGT    1080

GGCTCTGACG GGGAAAGGAC TGCGCCCTTT TGCTCCTGGT TCCAGGGAGT CCTGGGCATC    1140

CTGCGGTGTC GAGCAATAGC CTGGCTTCAG AGCTGAGAGT GCCTGGGGCC ACAGGAAAGG    1200

CAGGAACAGG ACCTTCTCTC TCCCAGGCCC AACGCAGGGG CCCTCACTGG CTGCAGCTGA    1260

TCTGTTTCCT TATACCAGAT CCTCAGTCTC ACTAAAGACA GCGATATGGG AGACACCCAG    1320

GGGCCTGGCC CGCCAGCCCA AAAGATGGTC ATCGGGAAGA GAAAAAGAAA AAAATGCTGC    1380

AGTTGTTCTC TCAAGCTAGG GCAGAAGAGG GGTGTCAACT CCTCAATAAA ATTT          1434
```

-continued (2) INFORMATION FOR SEQ ID NO: 3:

(i) SEQUENCE CHARACTERISTICS:
        (A) LENGTH: 344 amino acids
        (B) TYPE: amino acid
        (C) STRANDEDNESS: single
        (D) TOPOLOGY: linear (vii) IMMEDIATE SOURCE:
        (A) LIBRARY: LUNGTUT06
        (B) CLONE: 2551161

(xi) SEQUENCE DESCRIPTION: SEQ ID NO: 3:

```
Met Gly Phe Asn Leu Thr Phe His Leu Ser Tyr Lys Phe Arg Leu Leu
 1               5                  10                  15

Leu Leu Leu Thr Leu Cys Leu Thr Val Val Gly Trp Ala Thr Ser Asn
             20                  25                  30

Tyr Phe Val Gly Ala Ile Gln Glu Ile Pro Lys Ala Lys Glu Phe Met
         35                  40                  45

Ala Asn Phe His Lys Thr Leu Ile Leu Gly Lys Gly Lys Thr Leu Thr
 50                  55                  60

Asn Glu Ala Ser Thr Lys Lys Val Glu Leu Asp Asn Cys Pro Ser Val
 65                  70                  75                  80

Ser Pro Tyr Leu Arg Gly Gln Ser Lys Leu Ile Phe Lys Pro Asp Leu
             85                  90                  95

Thr Leu Glu Glu Val Gln Ala Glu Asn Pro Lys Val Ser Arg Gly Arg
            100                 105                 110

Tyr Arg Pro Gln Glu Cys Lys Ala Leu Gln Arg Val Ala Ile Leu Val
            115                 120                 125

Pro His Arg Asn Arg Glu Lys His Leu Met Tyr Leu Leu Glu His Leu
            130                 135                 140

His Pro Phe Leu Gln Arg Gln Leu Asp Tyr Gly Ile Tyr Val Ile
145                 150                 155                 160

His Gln Ala Glu Gly Lys Lys Phe Asn Arg Ala Lys Leu Leu Asn Val
            165                 170                 175

Gly Tyr Leu Glu Ala Leu Lys Glu Glu Asn Trp Asp Cys Phe Ile Phe
            180                 185                 190

His Asp Val Asp Leu Val Pro Glu Asn Asp Phe Asn Leu Tyr Lys Cys
            195                 200                 205

Glu Glu His Pro Lys His Leu Val Val Gly Arg Asn Ser Thr Gly Tyr
            210                 215                 220

Arg Leu Arg Tyr Ser Gly Tyr Phe Gly Gly Val Thr Ala Leu Ser Arg
225                 230                 235                 240

Glu Gln Phe Phe Lys Val Asn Gly Phe Ser Asn Asn Tyr Trp Gly Trp
            245                 250                 255

Gly Gly Glu Asp Asp Asp Leu Arg Leu Arg Val Glu Leu Gln Arg Met
            260                 265                 270

Lys Ile Ser Arg Pro Leu Pro Glu Val Gly Lys Tyr Thr Met Val Phe
            275                 280                 285

His Thr Arg Asp Lys Gly Asn Glu Val Asn Ala Glu Arg Met Lys Leu
            290                 295                 300

Leu His Gln Val Ser Arg Val Trp Arg Thr Asp Gly Leu Ser Ser Cys
305                 310                 315                 320

Ser Tyr Lys Leu Val Ser Val Glu His Asn Pro Leu Tyr Ile Asn Ile
            325                 330                 335

Thr Val Asp Phe Trp Phe Gly Ala
            340
```

(2) INFORMATION FOR SEQ ID NO: 4:

(i) SEQUENCE CHARACTERISTICS:
        (A) LENGTH: 2280 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT06
        (B) CLONE: 2551161

(xi) SEQUENCE DESCRIPTION: SEQ ID NO: 4:

```
GTGGATTTCC ACGGCTCTTG CCCAGAGGCG GGTACACTGT GTTCCAATGT GCCACGGAAC      60

TCACGCAGTG GCACTTTGTG GCTTCATGAA GGAAGAGGCA GGCCACGCAA CACTTCCTCC     120

CCAAGCCAAG GAGAAGTATC ACTTTTAGAG GCAGAGGAGC GGAAGGCAGT GGGTGTGACC     180

AAAAGTGCCA TTTGTTAAAG CTTATCTTCC TTGCCAGATT TTAAAAACTA TTATGGAAAA     240

TCTCAAGCAT TCACAAAAGT AGAGAGAAAG AAAGGACTCT CAGACTGTTG GAGCAGAACT     300

ACTGAGAAAA ACCAGGCATT GTATCTTCAG TTGTCATCAA GTTCGCAATC AGATTGGAAA     360

AGCTCAACTT GAAGCTTTCT TGCCTGCAGT GAAGCAGAGA GATAGATATT ATTCACGTAA     420

TAAAAAACAT GGGCTTCAAC CTGACTTTCC ACCTTTCCTA CAAATTCCGA TTACTGTTGC     480

TGTTGACTTT GTGCCTGACA GTGGTTGGGT GGGCCACCAG TAACTACTTC GTGGGTGCCA     540

TTCAAGAGAT TCCTAAAGCA AAGGAGTTCA TGGCTAATTT CCATAAGACC CTCATTTTGG     600

GGAAGGGAAA AACTCTGACT AATGAAGCAT CCACGAAGAA GGTAGAACTT GACAACTGTC     660

CTTCTGTGTC TCCTTACCTC AGAGGCCAGA GCAAGCTCAT TTTCAAACCA GATCTCACTT     720

TGGAAGAGGT ACAGGCAGAA AATCCCAAAG TGTCCAGAGG CCGGTATCGC CCTCAGGAAT     780

GTAAAGCTTT ACAGAGGGTC GCCATCCTCG TTCCCCACCG GAACAGAGAG AAACACCTGA     840

TGTACCTGCT GGAACATCTG CATCCCTTCC TGCAGAGGCA GCAGCTGGAT TATGGCATCT     900

ACGTCATCCA CCAGGCTGAA GGTAAAAAGT TTAATCGAGC CAAACTCTTG AATGTGGGCT     960

ATCTAGAAGC CCTCAAGGAA GAAAATTGGG ACTGCTTTAT ATTCCACGAT GTGGACCTGG    1020

TACCCGAGAA TGACTTTAAC CTTTACAAGT GTGAGGAGCA TCCCAAGCAT CTGGTGGTTG    1080

GCAGGAACAG CACTGGGTAC AGGTTACGTT ACAGTGGATA TTTTGGGGGT GTTACTGCCC    1140

TAAGCAGAGA GCAGTTTTTC AAGGTGAATG GATTCTCTAA CAACTACTGG GGATGGGGAG    1200

GCGAAGACGA TGACCTCAGA CTCAGGGTTG AGCTCCAAAG AATGAAAATT TCCCGGCCCC    1260

TGCCTGAAGT GGGTAAATAT ACAATGGTCT TCCACACTAG AGACAAAGGC AATGAGGTGA    1320

ACGCAGAACG GATGAAGCTC TTACACCAAG TGTCACGAGT CTGGAGAACA GATGGGTTGA    1380

GTAGTTGTTC TTATAAATTA GTATCTGTGG AACACAATCC TTTATATATC AACATCACAG    1440

TGGATTTCTG GTTTGGTGCA TGACCCTGGA TCTTTTGGTG ATGTTTGGAA GAACTGATTC    1500

TTTGTTTGCA ATAATTTTGG CCTAGAGACT TCAAATAGTA GCACACATTA GAACCTGTT     1560

ACAGCTCATT GTTGAGCTGA ATTTTTCCTT TTTGTATTTT CTTAGCAGAG CTCCTGGTGA    1620

TGTAGAGTAT AAAACAGTTG TAACAAGACA GCTTTCTTAG TCATTTTGAT CATGAGGGTT    1680

AAATATTGTA ATATGGATAC TTGAAGGACT TTATATAAAA GGATGACTCA AAGGATAAAA    1740

TGAACGCTAT TTGAGGACTC TGGTTGAAGG AGATTTATTT AAATTTGAAG TAATATATTA    1800

TGGGATAAAA GGCCACAGGA AATAAGACTG CTGAATGTCT GAGAGAACCA GAGTTGTTCT    1860

CGTCCAAGGT AGAAAGGTAC GAAGATACAA TACTGTTATT CATTTATCCT GTACAATCAT    1920
```

```
CTGTGAAGTG GTGGTGTCAG GTGAGAAGGC GTCCACAAAA GAGGGGAGAA AAGGCGACGA    1980

ATCAGGACAC AGTGAACTTG GGAATGAAGA GGTAGCAGGA GGGTGGAGTG TCGGCTGCAA    2040

AGGCAGCAGT AGCTGAGCTG GTTGCAGGTG CTGATAGCCT TCAGGGGAGG ACCTGCCCAG    2100

GTATGCCTTC CAGTGATGCC CACCAGAGAA TACATTCTCT ATTAGTTTTT AAAGAGTTTT    2160

TGTAAAATGA TTTTGTACAA GTAGGATATG AATTAGCAGT TTACAAGTTT ACATATTAAC    2220

TAATAATAAA TATGTCTATC AAATACCTCT GTAGTAAAAT GTGAAAAAGC AAAAAAAAAA    2280
```

(2) INFORMATION FOR SEQ ID NO: 5:

(i) SEQUENCE CHARACTERISTICS:
        (A) LENGTH: 325 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1150971

(xi) SEQUENCE DESCRIPTION: SEQ ID NO: 5:

```
Met Gln Ser Lys His Arg Lys Leu Leu Leu Arg Cys Leu Leu Val Leu
 1               5                  10                  15

Pro Leu Ile Leu Leu Val Asp Tyr Cys Gly Leu Leu Thr His Leu His
            20                  25                  30

Glu Leu Asn Phe Glu Arg His Phe His Tyr Pro Leu Asn Asp Asp Thr
        35                  40                  45

Gly Ser Gly Ser Ala Ser Ser Gly Leu Asp Lys Phe Ala Tyr Leu Arg
    50                  55                  60

Val Pro Ser Phe Thr Ala Glu Val Pro Val Asp Gln Pro Ala Arg Leu
65                  70                  75                  80

Thr Met Leu Ile Lys Ser Ala Val Gly Asn Ser Arg Arg Arg Glu Ala
                85                  90                  95

Ile Arg Arg Thr Trp Gly Tyr Glu Gly Arg Phe Ser Asp Val His Leu
            100                 105                 110

Arg Arg Val Phe Leu Leu Gly Thr Ala Glu Asp Ser Glu Lys Asp Val
        115                 120                 125

Ala Trp Glu Ser Arg Glu His Gly Asp Ile Leu Gln Ala Asp Phe Thr
    130                 135                 140

Asp Ala Tyr Phe Asn Asn Thr Leu Lys Thr Met Leu Gly Met Arg Trp
145                 150                 155                 160

Ala Ser Glu Gln Phe Asn Arg Ser Glu Phe Tyr Leu Phe Val Asp Asp
                165                 170                 175

Asp Tyr Tyr Val Ser Ala Lys Asn Val Leu Lys Phe Leu Gly Arg Gly
            180                 185                 190

Arg Gln Ser His Gln Pro Glu Leu Leu Phe Ala Gly His Val Phe Gln
        195                 200                 205

Thr Ser Pro Leu Arg His Lys Phe Ser Lys Trp Tyr Val Ser Leu Glu
    210                 215                 220

Glu Tyr Pro Phe Asp Arg Trp Pro Pro Tyr Val Thr Ala Gly Ala Phe
225                 230                 235                 240

Ile Leu Ser Gln Lys Ala Leu Arg Gln Leu Tyr Ala Ala Ser Val His
                245                 250                 255

Leu Pro Leu Phe Arg Phe Asp Asp Val Tyr Leu Gly Ile Val Ala Leu
            260                 265                 270
```

```
Lys Ala Gly Ile Ser Leu Gln His Cys Asp Asp Phe Arg Phe His Arg
            275                 280                 285

Pro Ala Tyr Lys Gly Pro Asp Ser Tyr Ser Val Ile Ala Ser His
            290                 295                 300

Glu Phe Gly Asp Pro Glu Met Thr Arg Val Trp Asn Glu Cys Arg
305                 310                 315                 320

Ser Ala Asn Tyr Ala
            325
```

(2) INFORMATION FOR SEQ ID NO: 6:

(i) SEQUENCE CHARACTERISTICS:
        (A) LENGTH: 326 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 2745735

(xi) SEQUENCE DESCRIPTION: SEQ ID NO: 6:

```
Met Ala Ser Lys Val Ser Cys Leu Tyr Val Leu Ser Val Val Cys Trp
1               5                   10                  15

Ala Ser Ala Leu Trp Tyr Leu Ser Ile Thr Arg Pro Thr Ser Ser Tyr
            20                  25                  30

Thr Gly Ser Lys Pro Phe Ser His Leu Thr Val Ala Arg Lys Asn Phe
            35                  40                  45

Thr Phe Gly Asn Ile Arg Thr Arg Pro Ile Asn Pro His Ser Phe Glu
50                  55                  60

Phe Leu Ile Asn Glu Pro Asn Lys Cys Glu Lys Asn Ile Pro Phe Leu
65                  70                  75                  80

Val Ile Leu Ile Ser Thr Thr His Lys Glu Phe Asp Ala Arg Gln Ala
            85                  90                  95

Ile Arg Glu Thr Trp Gly Asp Glu Asn Asn Phe Lys Gly Ile Lys Ile
            100                 105                 110

Ala Thr Leu Phe Leu Leu Gly Lys Asn Ala Asp Pro Val Leu Asn Gln
            115                 120                 125

Met Val Glu Gln Glu Ser Gln Ile Phe His Asp Ile Ile Val Glu Asp
130                 135                 140

Phe Ile Asp Ser Tyr His Asn Leu Thr Leu Lys Thr Leu Met Gly Met
145                 150                 155                 160

Arg Trp Val Ala Thr Phe Cys Ser Lys Ala Lys Tyr Val Met Lys Thr
            165                 170                 175

Asp Ser Asp Ile Phe Val Asn Met Asp Asn Leu Ile Tyr Lys Leu Leu
            180                 185                 190

Lys Pro Ser Thr Lys Pro Arg Arg Arg Tyr Phe Thr Gly Tyr Val Ile
            195                 200                 205

Asn Gly Gly Pro Ile Arg Asp Val Arg Ser Lys Trp Tyr Met Pro Arg
            210                 215                 220

Asp Leu Tyr Pro Asp Ser Asn Tyr Pro Pro Phe Cys Ser Gly Thr Gly
225                 230                 235                 240

Tyr Ile Phe Ser Ala Asp Val Ala Glu Leu Ile Tyr Lys Thr Ser Leu
            245                 250                 255

His Thr Arg Leu Leu His Leu Glu Asp Val Tyr Val Gly Leu Cys Leu
            260                 265                 270

Arg Lys Leu Gly Ile His Pro Phe Gln Asn Ser Gly Phe Asn His Trp
```

```
                   275                 280                 285

Lys Met Ala Tyr Ser Leu Cys Arg Tyr Arg Val Ile Thr Val His
    290                 295                 300

Gln Ile Ser Pro Glu Glu Met His Arg Ile Trp Asn Asp Met Ser Ser
305                 310                 315                 320

Lys Lys His Leu Arg Cys
                325

(2) INFORMATION FOR SEQ ID NO: 7:

(i) SEQUENCE CHARACTERISTICS:
        (A) LENGTH: 362 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1469908

(xi) SEQUENCE DESCRIPTION: SEQ ID NO: 7:

Met Lys Glu Pro Ala Leu Pro Gly Thr Ser Leu Gln Arg Ala Cys Arg
1               5                   10                  15

Leu Leu Val Ala Phe Cys Ala Leu His Leu Ser Ala Thr Leu Leu Tyr
                20                  25                  30

Tyr Leu Ala Gly Ser Ser Leu Thr Pro Pro Arg Ser Pro Glu Pro Pro
            35                  40                  45

Pro Arg Arg Pro Pro Ala Asn Leu Ser Leu Pro Pro Ser Arg Pro
    50                  55                  60

Pro Pro Pro Pro Ala Ala Arg Pro Arg Pro Gly Pro Val Ser Ala Gln
65                  70                  75                  80

Pro Arg Asn Leu Pro Asp Ser Ala Pro Ser Gly Leu Cys Pro Asp Pro
                85                  90                  95

Ser Pro Leu Leu Val Gly Pro Leu Arg Val Glu Phe Ser Gln Pro Val
            100                 105                 110

Asn Leu Glu Glu Val Ala Ser Thr Asn Pro Glu Val Arg Glu Gly Gly
        115                 120                 125

Arg Phe Ala Pro Lys Asp Cys Lys Ala Leu Gln Lys Val Ala Ile Ile
130                 135                 140

Ile Pro Phe Arg Asn Arg Glu Glu His Leu Lys Tyr Trp Leu Tyr Tyr
145                 150                 155                 160

Met His Pro Ile Leu Gln Arg Gln Gln Leu Asp Tyr Gly Val Tyr Val
                165                 170                 175

Ile Asn Gln Asp Gly Asp Glu Glu Phe Asn Arg Ala Lys Leu Leu Asn
            180                 185                 190

Val Gly Phe Thr Glu Ala Leu Lys Glu Tyr Asp Tyr Asp Cys Phe Val
        195                 200                 205

Phe Ser Asp Val Asp Leu Ile Pro Met Asp Asp Arg Asn Thr Tyr Lys
210                 215                 220

Cys Tyr Ser Gln Pro Arg His Leu Ser Val Ser Met Asp Lys Phe Gly
225                 230                 235                 240

Phe Arg Leu Pro Tyr Asn Gln Tyr Phe Gly Gly Val Ser Ala Leu Ser
                245                 250                 255

Lys Glu Gln Phe Thr Lys Ile Asn Gly Phe Pro Asn Asn Tyr Trp Gly
            260                 265                 270

Trp Gly Gly Glu Asp Asp Asp Ile Tyr Asn Arg Leu Val Phe Lys Gly
        275                 280                 285
```

```
                                    -continued

Met Gly Ile Ser Arg Pro Asp Ala Val Ile Gly Lys Cys Arg Met Ile
    290                 295                 300

Arg His Ser Arg Asp Arg Lys Asn Glu Pro Asn Pro Glu Arg Phe Asp
305                 310                 315                 320

Arg Ile Ala His Thr Arg Glu Thr Met Ser Ser Asp Gly Leu Asn Ser
                325                 330                 335

Leu Ser Tyr Glu Val Leu Arg Thr Asp Arg Phe Pro Leu Tyr Thr Arg
            340                 345                 350

Ile Thr Val Asp Ile Gly Ala Pro Gly Ser
            355                 360
```